United States Patent [19]

Siren et al.

[11] Patent Number: 5,330,979
[45] Date of Patent: Jul. 19, 1994

[54] METHOD OF TREATING RENAL DISORDERS WITH INOSITOLTRIPHOSPHATE

[75] Inventors: Matti Siren, Montagnola/Lugano, Switzerland; Bertil Lofkvist, Perstorp; Lars Edvinsson, Lund, both of Sweden

[73] Assignee: Perstorp AB, Perstorp, Sweden

[21] Appl. No.: 900,129

[22] Filed: Jun. 18, 1992

Related U.S. Application Data

[63] Continuation-in-part of Ser. No. 580,661, Sep. 11, 1990, Pat. No. 5,128,332, which is a continuation-in-part of Ser. No. 492,740, Mar. 13, 1990, Pat. No. 5,015,634, which is a continuation-in-part of Ser. No. 367,968, Jun. 19, 1989, Pat. No. 5,051,411, which is a continuation-in-part of Ser. No. 251,566, Sep. 30, 1988, Pat. No. 5,023,248, which is a continuation-in-part of Ser. No. 214,500, Jul. 1, 1988, Pat. No. 5,003,098, which is a continuation-in-part of Ser. No. 173,985, Mar. 28, 1988, Pat. No. 5,019,566, which is a continuation-in-part of Ser. No. 38,230, Apr. 14, 1987, abandoned, which is a continuation-in-part of Ser. No. 15,679, Feb. 17, 1987, Pat. No. 4,797,390, which is a continuation-in-part of Ser. No. 788,801, Oct. 18, 1985, Pat. No. 4,735,936.

[30] Foreign Application Priority Data

Oct. 23, 1984 [SE] Sweden .................................. 8405295
Dec. 16, 1986 [SE] Sweden .................................. 8601709

[51] Int. Cl.$^5$ .............................................. A61K 31/66
[52] U.S. Cl. ..................................................... 514/103
[58] Field of Search ......................................... 514/103

[56] References Cited

FOREIGN PATENT DOCUMENTS 0179439 10/1985 European Pat. Off. .
0359257 9/1989 European Pat. Off. .

*Primary Examiner*—Marianne M. Cintins
*Assistant Examiner*—T. J. Criares
*Attorney, Agent, or Firm*—Scully, Scott, Murphy & Presser

[57] ABSTRACT

A method of preventing or alleviating renal disorders by administering to a human or an animal in need thereof a pharmaceutical composition comprising an effective amount amount of at least one specific isomer of inositol trisphosphate sufficient to obtain said prevention or alleviation.

11 Claims, No Drawings

METHOD OF TREATING RENAL DISORDERS WITH INOSITOLTRIPHOSPHATE

REFERENCE TO RELATED APPLICATIONS

This is a continuation-in-part of U.S. patent application, Ser. No. 580,661 filed Sep. 11, 1990, now U.S. Pat. No. 5,128,332, which is a continuation-in-part of U.S. patent application, Ser. No. 492,740, filed Mar. 13, 1990, now U.S. Pat. No. 5,015,634, which is a continuation-in-part of U.S. patent application, Ser. No. 367,968, filed Jun. 19, 1989, now U.S. Pat. No. 5,051,411, which is a continuation-in-part of U.S. patent application, Ser. No. 251,566, which is a continuation-in-part filed Sep. 30, 1988, now U.S. Pat. No. 5,023,248; U.S. patent applications, Ser. No. 214,500 filed Jul. 1, 1988, now U.S. Pat. No. 5,003,098; which is a continuation-in-part of U.S. patent application, Ser. No. 173,985 filed Mar. 28, 1988, now U.S. Pat. No. 5,019,566; which is a continuation-in-part of U.S. patent application Ser. No. 038,230, now Apr. 14, 1987, now abandoned, which is a continuation-in-part of U.S. patent application Ser. No. filed Feb. 17, 1987 now U.S. Pat. No. 4,797,390, which is a continuation-in-part of U.S. patent application Ser. No. 788,801, filed Oct. 18, 1985 now U.S. Pat. No. 4,735,936.

FIELD OF THE INVENTION

The present invention relates to a method of preventing or alleviating different conditions in the body by administering thereto a pharmaceutical composition comprising an amount of at least one specific isomer of inositoltriphosphate sufficient to obtain said prevention or alleviation.

Neuropeptide Y (NPY) is a peptide widely distributed in the central and peripheral nervous system. The peptide co-exists with nonadrenaline in many neurons and as a neurotransmitter per se or synergistically together with noradrenaline. NPY-containing fibres are numerous around arteries especially for arteries in the heart but also arteries in the respiratory tract, the gastrointestinal tract and genitourinary tract. NPY is also present in the cerebral area with effects on e.g. blood pressure and release of different hormones.

NPY per se has vasoconstrictor effects, i.e. there is observed an increased blood pressure, local vasoconstriction and reduced heart rate when the substance is infused to animals.

NPY belongs to the pancreatic polypeptide (PP) family which also includes for example peptide YY (PYY).

In man and animals abnormal NPY-levels are associated with the following diseases or conditions:

Diseases pertaining to the heart, blood vessels or the renal system such as vasospasm, angina, hemorrhage, high blood pressure, cardiac hypertrophy, myocardial infarction and abnormal renal conditions like impaired flow of fluid;

Cerebral diseases and diseases related to the central nervous system such as stroke and conditions associated with stroke, cerebral vassopassage hemorrhage and depression.

Abnormal drink and food intake such as obesity;
Diabetes or complications of diabetes;
Inflammatory diseases such as arthritis;
Respiratory diseases such as asthma;

When for example well-known drugs effective against hypertension such as β-blockers are used to control the blood pressure, the raised level of NPY is not normalized. This phenomenon may be one important reason for the increased incidence of people with high blood pressure to get secondary cardiovascular complications. There are no compounds known to antagonize NPY or the effects of NPY.

From the U.S. Pat. No. 4,735,936 a pharmaceutical composition comprising as a pharmaceutically active ingredient at least one isomer of inositoltrisphosphate is known. In said patent the effect of this pharmaceutical composition is shown for different areas, such as arthritis.

SUMMARY OF THE INVENTION

According to the present invention it has surprisingly become possible to overcome and reduce the above mentioned injuries and disorders as a method of preventing or alleviating these conditions has been brought about. At said method a pharmaceutical compostion comprising an amount of at least one specific isomer of inositoltrisphosphate (IP$_3$) sufficient to obtain said prevention or alleviation is administered to a human or an animal.

Preferred embodiments of the invention relate to a method of preventing or alleviating conditions of abnormal levels of NPY by administering to a human or an animal a pharmaceutical composition comprising an amount of at least one specific isomer of IP$_3$ sufficient to obtain said prevention or alleviation. These conditions are in particular related to the cardiovascular, renal and cerebral disorders and diseases.

In addition the present invention also covers a method of preventing or alleviating cardiovascular, renal and/or cerebral diseases by administering to a human or animal a pharmaceutical composition comprising at least one isomer of inositoltrisphosphate and another pharmaceutically active compound effective in the cardiovascular, renal and/or cerebral area sufficient to obtain said prevention or alleviation.

DETAILED DESCRIPTION OF PREFERRED EMBODIMENTS

As examples of conditions, which the method according to the invention is useful to prevent or alleviate, there are mentioned the following conditions:

Diseases pertaining to the heart, blood vessels or the renal system such as vasospasm, heart failure, shock, cardiac hypertrophy, increased blood pressure, atherosclerosis, angina, myocardial infarction, sudden cardiac death, arrythmia, hemorrhage, peripheral vascular diseases and abnormal renal conditions such as impaired flow of fluid and renal failure; cerebral diseases and diseases related to the central nervous system such as cerebral infarction, stroke and conditions related to stroke, cerebral vasospasm and hemorrhage, depression and dementia;

Conditions related to increased sympathetic nerve activity for example during or after coronary artery surgery and operations and surgery in the gastrointestinal tract;

Diseases related to abnormal gastrointestinal mobility and secretion such as different forms of ileus, diarrhea and Chron's disease;

Abnormal drink and food intake such as obesity, anorexia and metabolic disorders;

Respiratory diseases such as asthma or conditions related to asthma;

Diseases related to abnormal hormone release for example from the pituitary;

Abnormal levels of NPY are associated with the above mentioned disorders and $IP_3$ is active primarily as an NPY-antagonist or as antagonist against NPY-induced effects. Peptides which are related to NPY such as peptide YY (PYY) and/or other peptides belonging to the pancreatic polypeptide-fold (PP-fold) family of regulatory peptides also occuring normally in some of the conditions mentioned above. Under certain circumstances the effect of $IP_3$ could also be directed against properties or effects induced by these peptides. In some conditions the effects could be mediated by substances such as endothelin and the like.

However, $IP_3$ is also effective against these conditions by other mode of action.

The production of $IP_3$ and the isolation of the different isomers thereof are disclosed in the U.S. Pat. No. 4.777.134. The $IP_3$ isomers can also be produced by synthetic methods, chemically or enzymatically, starting with e.g. inositol and a phosphorus source. Furthermore, microbiological production methods including hybrid DNA-techniques of $IP_3$ are also suitable.

The structure of $IP_3$ and the different isomers thereof are disclosed in the U.S. Pat. No. 4,735,936 and the U.S. Pat. No. 4,797,390.

It is suitable that the composition used according to the invention exists in unit dosage form. Tablets, granules or capsules are suitable administration forms for such unit dosage. Furthermore, tablets and granules can easily be surface treated such as to provide an enteric coating to prevent an uncontrolled hydrolysis in the stomach and to bring about a desired absorption in the intestine. Other suitable administration forms are slow release and transdermal administration, nasal, rectal, intraarticular, topical, intraperitoneal, and subcutaneous administrations. A usual pharmaceutically cceptable additive, excipient and/or carrier can be included in the medicament. The tablets or granules can also contain a disintegrant which causes the tablets or the granules, respectively, to disintegrate easily in the intestine. In certain cases, especially in acute situations, it is preferable to use the unit dosage in the form of a solution for intravenous administration.

The pharmaceutical composition used in the method can also consist as such of $IP_3$ solely without any additive, excipient or carrier.

If desired, the composition can be free of other inositol phosphates, $IP_1$, $IP_2$, $IP_4$, $IP_5$ and $IP_6$. Accordingly, the mixture of $IP_3$ isomers can have a purity of 90-100% , such as 93-100% or preferably 95-100%.

Alternatively, the pharmaceutical composition used in the method can consist of or comprise one or more specific $IP_3$ isomers, each present in substantially pure form. Thus, the different isomers can be isolated from each other in substantially pure form, which means that they have a purity of 80-100%, such as 82-100% or 85-100%, preferably 90-100%. Since the isomers can be produced in pure form they can be mixed in any proportion, of course.

The composition can consist of $IP_3$, wherein said $IP_3$ is provided by at least one of $IP_6$, $IP_5$ or $IP_4$ and a degradative substance such as an enzyme suitable to form $IP_3$.

It is in most cases suitable that the $IP_3$-isomer or isomers in the composition used in the method according to the invention is present in salt form in order not to affect the mineral balance negatively. The salt should preferably consist of a sodium, potassium, calcium, zinc or magnesium salt or a mixture of two or more of these salts.

For administration to human patients appropriate dosages can routinely be determined by those skilled in this art by extension of the results obtained in animals at various dosages. The preferred dosage for humans falls within the range of 0.1 to 1000 mg, especially 0.1-200 mg $IP_3$/day/kg body weight.

The pharmaceutical composition used in the method according to the invention usually contains 0.01-1.5 g, such as 0.05-1.3 g or preferably 0.1-1 g of $IP_3$ per unit dosage.

The composition used according to the present invention contains at least one, sometimes two or more of the following substances, which correspond to the essential $IP_3$-isomer or isomers mentioned above:

D-myo-inositol-1,2,6-trisphosphate of the formula

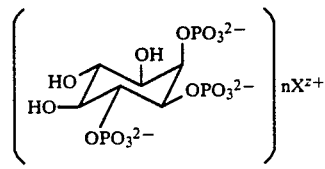

where X is hydrogen, at least one univalent, divalent or multivalent cation, or a mixture thereof, n is the number of ions, and z is the charge of the respectively ion;

myo-inositol-1,2,3.-trisphosphate of the formula

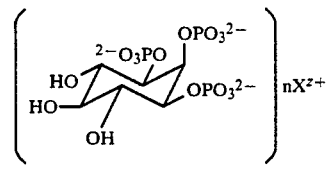

where X, n and z have the above mentioned meaning;

L-myo-inositol-1,3,4-trisphosphate of the formula

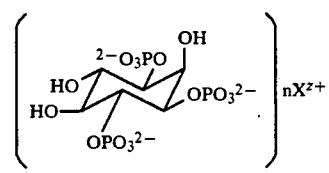

where X, n and z have the above mentioned meaning.

In each of the above formulas n ranges between 6 to 1 inclusive and z ranges from 1 to 6 inclusive. Preferably, n is between 3 to 6 inclusive and z is 3, 2 or 1. Of above isomers D-myo-inositol-1,2,6-trisphosphate is preferred.

Other inositol trisphosphate isomers that may be utilized in the present invention as the active $IP_3$ ingredient in the composition have the structural formula

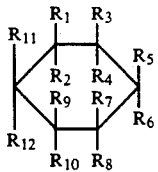
(I)

One group of inositol trisphosphate compounds is defined by the structural formula (I) where three of $R_1$, $R_3$, $R_5$, $R_7$, $R_{10}$ and $R_{11}$ are hydroxyl and the remaining three are phosphate and $R_2$, $R_4$, $R_6$, $R_8$, $R_9$ and $R_{12}$ are hydrogen.

Another group of inositol trisphosphates is defined by the structural formula (I) where three of $R_1$, $R_3$, $R_6$, $R_7$, $R_9$ and $R_{12}$ are hydroxyl and the remaining three are phosphate and $R_2$, $R_4$, $R_5$, $R_8$, $R_{10}$ and $R_{11}$ are hydrogen.

Still another group of inositol trisphosphates is defined by the structural formula (I) where three of $R_1$, $R_3$, $R_5$, $R_8$, $R_{10}$ and $R_{12}$ are hydroxyl and the remaining three are phosphate and $R_2$, $R_4$, $R_6$, $R_7$, $R_9$ and $R_{11}$ are hydrogen.

Yet another group of inositol trisphosphates is defined by the structural formula (I) where three of $R_1$, $R_4$, $R_5$, $R_8$, $R_9$ and $R_{12}$ are hydroxyl and the remaining three are phosphate and $R_2$, $R_3$, $R_6$, $R_7$, $R_{10}$ and $R_{11}$ are hydrogen.

Still yet another group of inositol trisphosphates is defined by the structural formula (I) where three of $R_1$, $R_3$, $R_6$, $R_8$, $R_9$ and $R_{12}$ are hydroxyl and the remaining three are phosphate and $R_2$, $R_4$, $R_5$, $R_7$, $R_{10}$ and $R_{11}$ are hydrogen.

Even still another group of inositol trisphosphates is defined by the structural formula (I) where three of $R_1$, $R_3$, $R_6$, $R_7$, $R_{10}$ and $R_{12}$ are hydroxyl and the remaining three are phosphate and $R_2$, $R_4$, $R_5$, $R_8$, $R_9$ and $R_{11}$ are hydrogen.

Even yet another group of inositol trisphosphates is defined by the structural formula (I) where three of $R_1$, $R_3$, $R_5$, $R_8$, $R_{10}$ and $R_{11}$ are hydroxyl and the remaining three are phosphate and $R_2$, $R_4$, $R_6$, $R_7$, $R_9$ and $R_{12}$ are hydrogen.

Finally, another group of inositol trisphosphates is defined by the structural formula (I) where three of $R_1$, $R_3$, $R_5$, $R_7$, $R_9$ and $R_{11}$ are hydroxyl and the remaining three are phosphate and $R_2$, $R_4$, $R_6$, $R_8$, $R_{10}$ and $R_{12}$ are hydrogen.

Particular inositol trisphosphate compounds within the contemplation of the above formula include compounds having the structural formula (I) where $R_5$, $R_7$ and $R_{10}$ are phosphate, $R_1$, $R_3$ and $R_{11}$ are hydroxyl and $R_2$, $R_4$, $R_6$, $R_8$, $R_9$ and $R_{12}$ are hydrogen;

$R_1$, $R_{10}$ and $R_{11}$ are phosphate, $R_3$, $R_5$ and $R_7$ are hydroxyl and $R_2$, $R_4$, $R_6$, $R_8$, $R_9$ and $R_{12}$ are hydrogen;

$R_1$, $R_3$ and $R_{11}$ are phosphate, $R_5$, $R_7$ and $R_{10}$ are hydroxyl and $R_2$, $R_4$, $R_6$, $R_8$, $R_9$ and $R_{12}$ are hydrogen;

$R_3$, $R_5$ and $R_7$ are phosphate, $R_1$, $R_{10}$ and $R_{11}$ are hydroxyl and $R_2$, $R_4$, $R_6$, $R_8$, $R_9$ and $R_{12}$ are hydrogen;

$R_3$, $R_7$ and $R_{10}$ are phosphate, $R_1$, $R_5$ and $R_{11}$ are hydroxyl and $R_2$, $R_4$, $R_6$, $R_8$, $R_9$ and $R_{12}$ are hydrogen;

$R_3$, $R_{10}$ and $R_{11}$ are phosphate, $R_1$, $R_5$ and $R_7$ are hydroxyl and $R_2$, $R_4$, $R_6$, $R_8$, $R_9$ and $R_{12}$ are hydrogen;

$R_1$, $R_3$ and $R_6$ are phosphate, $R_7$, $R_9$ and $R_{12}$ are hydroxyl and $R_2$, $R_4$, $R_5$, $R_8$, $R_{10}$ and $R_{11}$ are hydrogen;

$R_6$, $R_7$ and $R_9$ are phosphate, $R_1$, $R_3$ and $R_{12}$ are hydroxyl and $R_2$, $R_4$, $R_5$, $R_8$, $R_{10}$ and $R_{11}$ are hydrogen;

$R_3$, $R_5$ and $R_8$ are phosphate, $R_1$, $R_{10}$ and $R_{12}$ are hydroxyl and $R_2$, $R_4$, $R_6$, $R_7$, $R_9$ and $R_{11}$ are hydrogen;

$R_1$, $R_3$ and $R_{12}$ are phosphate, $R_5$, $R_8$ and $R_{10}$ are hydroxyl and $R_2$, $R_4$, $R_6$, $R_7$, $R_9$ and $R_{11}$ are hydrogen;

$R_1$ $R_3$ and $R_5$ are phosphate, $R_8$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_8$ are phosphate, $R_3$, $R_{10}$ and $R_{12}$ are hydroxyl and $R_2$, $R_4$, $R_6$, $R_7$, $R_9$ and $R_{11}$ are hydrogen;

$R_1$, $R_5$ and $R_{12}$ are phosphate, $R_3$, $R_8$ and $R_{10}$ are hydroxyl and $R_2$, $R_4$, $R_6$, $R_7$, $R_9$ and $R_{11}$ are hydrogen;

$R_1$, $R_3$ and $R_{12}$ are phosphate, $R_6$, $R_8$ and $R_9$ are hydroxyl and $R_2$, $R_4$, $R_5$, $R_7$, $R_{10}$ and $R_{11}$ are hydrogen;

$R_1$, $R_3$ and $R_6$ are phosphate, $R_7$, $R_{10}$ and $R_{12}$ are hydroxyl and $R_2$, $R_4$, $R_5$, $R_8$, $R_9$ and $R_{11}$ are hydrogen;

$R_4$, $R_5$ and $R_8$ are phosphate, $R_1$, $R_9$ and $R_{12}$ are hydroxyl and $R_2$, $R_3$, $R_6$, $R_7$, $R_{10}$ and $R_{11}$ are hydrogen;

$R_3$, $R_5$ and $R_8$ are phosphate, $R_1$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_8$, $R_{10}$ and $R_{11}$ are hydroxyl and $R_2$, $R_4$, $R_6$, $R_7$, $R_9$ and $R_{12}$ are hydrogen;

$R_1$, $R_3$ and $R_5$ are phosphate, $R_7$, $R_9$ and $R_{11}$ are hydroxyl and $R_2$, $R_4$, $R_6$, $R_8$, $R_{10}$ and $R_{12}$ are hydrogen;

$R_1$, $R_3$ and $R_{12}$ are phosphate, $R_5$, $R_8$ and $R_9$ are hydroxyl and $R_2$, $R_4$, $R_6$, $R_7$, $R_{10}$ and $R_{11}$ are hydrogen;

$R_1$, $R_3$ and $R_8$ are phosphate, $R_5$, $R_9$ and $R_{12}$ are hydroxyl and $R_2$, $R_4$, $R_6$, $R_7$, $R_{10}$ and $R_{11}$ are hydrogen;

$R_3$, $R_5$ and $R_{12}$ are phosphate, $R_1$, $R_8$ and $R_9$ are hydroxyl and $R_2$, $R_4$, $R_6$, $R_7$, $R_{10}$ and $R_{11}$ are hydrogen;

$R_1$, $R_5$ and $R_9$ are phosphate, $R_3$, $R_8$ and $R_{12}$ are hydroxyl and $R_2$, $R_4$, $R_6$, $R_7$, $R_{10}$ and $R_{11}$ are hydrogen;

$R_1$, $R_5$ and $R_{12}$ are phosphate, $R_3$, $R_8$ and $R_9$ are hydroxyl and $R_2$, $R_4$, $R_6$, $R_7$, $R_{10}$ and $R_{11}$ are hydrogen;

$R_1$, $R_3$ and $R_9$ are phosphate, $R_5$, $R_8$ and $R_{12}$ are hydroxyl and $R_2$, $R_4$, $R_6$, $R_7$, $R_{10}$ and $R_{11}$ are hydrogen;

$R_3$, $R_5$ and $R_9$ are phosphate, $R_1$, $R_8$ and $R_{12}$ are hydroxyl and $R_2$, $R_4$, $R_6$, $R_7$, $R_{10}$ and $R_{11}$ are hydrogen;

$R_5$, $R_9$ and $R_{12}$ are phosphate, $R_1$, $R_3$ and $R_8$ are hydroxyl and $R_2$, $R_4$, $R_6$, $R_7$, $R_{10}$ and $R_{11}$ are hydrogen;

$R_1$, $R_8$ and $R_9$ are phosphate, $R_3$, $R_5$ and $R_{12}$ are hydroxyl and $R_2$, $R_4$, $R_6$, $R_7$, $R_{10}$ and $R_{11}$ are hydrogen;

$R_1$, $R_8$ and $R_{12}$ are phosphate, $R_3$, $R_5$ and $R_9$ are hydroxyl and $R_2$, $R_4$, $R_6$, $R_7$, $R_{10}$ and $R_{11}$ are hydrogen;

$R_5$, $R_8$ and $R_{12}$ are phosphate, $R_1$, $R_3$ and $R_9$ are hydroxyl and $R_2$, $R_4$, $R_6$, $R_7$, $R_{10}$ and $R_{11}$ are hydrogen;

$R_1$, $R_9$ and $R_{12}$ are phosphate, $R_3$, $R_5$ and $R_8$ are hydroxyl and $R_2$, $R_4$, $R_6$, $R_7$, $R_{10}$ and $R_{11}$ are hydrogen;

$R_5$, $R_8$ and $R_9$ are phosphate, $R_1$, $R_3$ and $R_{12}$ are hydroxyl and $R_2$, $R_4$, $R_6$, $R_7$, $R_{10}$ and $R_{11}$ are hydrogen;

$R_3$, $R_8$ and $R_9$ are phosphate, $R_1$, $R_5$ and $R_{12}$ are hydroxyl and $R_2$, $R_4$, $R_6$, $R_7$, $R_{10}$ and $R_{11}$ are hydrogen;

$R_3$, $R_8$ and $R_{12}$ are phosphate, $R_1$, $R_5$ and $R_{12}$ are hydroxyl and $R_2$, $R_4$, $R_6$, $R_7$, $R_{10}$ and $R_{11}$ are hydrogen;

$R_3$, $R_8$ and $R_{12}$ are phosphate, $R_1$, $R_5$ and $R_9$ are hydroxyl and $R_2$, $R_4$, $R_6$, $R_7$, $R_{10}$ and $R_{11}$ are hydrogen;

$R_8$, $R_9$ and $R_{12}$ are phosphate, $R_1$, $R_3$ and $R_5$ are hydroxyl and $R_2$, $R_4$, $R_6$, $R_7$, $R_{10}$ and $R_{11}$ are hydrogen.

The above formula describes specific isomers of inositol trisphosphate where the inositol is selected from the group myoinositol, cisinositol, epiinositol, alloinositol, neoinositol, mucoinositol, chiroinositol and scylloinositol.

$IP_3$ may be sole pharmaceutically active ingredient in the composition used. However, also other pharmaceutically active ingredients can be present therein. The amount of $IP_3$ should then constitute 5 to 95 or 15 to 80, such as 25 to 60 percent by weight of said active ingredients.

The present invention also covers a method of preventing or alleviating cardiovascular, renal and/or cerebral diseases by administering to a human or an animal a pharmaceutical composition comprising at least one isomer of inositoltrisphosphate and another pharmaceutically active compound effective in the cardiovascular, renal and/or cerebral area sufficient to obtain said prevention or alleviation.

As examples of conditions which the method according to this embodiment of the invention is useful to prevent or alleviate there are mentioned the following conditions:

Cardiovascular diseases such as vasospasm, angina, heart failure, shock, hypertension and myocardial infarction;

Renal diseases such as impaired flow of fluid and renal failure;

Cerebral diseases such as cerebral infarction, stroke or conditions related to stroke, cerebral vasospasm and hemorrhage;

Diseases related to the central nervous system such as dementia and depression.

In preferred embodiments of this type of the invention the other pharmaceutically active component is selected from the group of α-adrenergic blocking agent, β-adrenergic blocking agents, calcium-channel blockers, ACE-inhibitors and diuretics. As specific examples of this type of compounds the following could be mentioned: Phenoxybenzamine, phentolamine and prazosin; propranolol, metaprolol and atenolol; verapamil and nifedipine; captopril and enalapril; benzthiazide and furosemide.

In one preferred embodiment of this type of the invention the composition comprises at least one isomer of $IP_3$ in addition to an anti-hypertension drug.

One function of $IP_3$ is to regulate the NPY-related components of the diseases which are not affected by any of the above mentioned pharmaceutically active agents. A proper regulation of the NPY-related components of a disease has many beneficial effects. For example the incidence of secondary cardiovascular disorders are increased in patients with hypertension although their blood pressure is controlled by normal therapy. When the NPY-component of the disease is controlled by the presence of $IP_3$ the incidence of secondary complications are reduced.

When the pharmaceutical composition comprises $IP_3$ and another pharmaceutically active compound the dosage form could be combined or separate for separate or combined administration.

The invention will be further explained in connection with the following examples. Example 1 shows the counteractive effect of $IP_3$ against NPY-induced vasoconstriction. Example 2 demonstrates the reduction of NPY-induced hypertension in vivo when $IP_3$ is administered. Example 3 illustrates the preparation of an injectable solution of $IP_3$. Example 4 relates to the inhibition of gastrointestinal secretion after treatment with $IP_3$.

EXAMPLE 1

The basilar arteries from guinea pigs were dissected free and were then cut into cylindrical segments (2-3 mm long; 0.2-0.3 mm outer diameter) before the experiments started. Each segment was mounted on two L-shaped metal prongs, where one was connected to a force displacement transducer for continuous recording of the tension and the other to a displacement device.

The mounted specimens were immersed in tissue baths (37° C.) containing a buffer solution of the following composition (mM) and pH 7.4: sodium chloride, 119; sodium hydrogen carbonate, 15; potassium chloride, 4.6; magnesium chloride, 1,2; sodium dihydrogen phosphate, 1.2; calcium chloride, 1.5; glucose, 11.

A tension of 2 mN was applied to the arterial segments and the contractile capacity of each vessel segment was examined by exposure to a potassium-rich (60 mM) buffer solution. The maximum contraction obtained in this way was given the value 100%.

The NPY-induced contraction was measured after dissolving NPY in the above mentioned buffer to a final concentration of 0.3 μM NPY.

The antagonistic properties of D-myo-inositol-1.2.6-trisphosphate ($IP_3$) in this system were evaluated by incubation with different concentrations of $IP_3$ twenty minutes before the addition of NPY to the tissue bath. The following results were obtained:

| Compound | Contraction (%) |
|---|---|
| NPY, no $IP_3$ | 76.4 |
| NPY + $IP_3$ ($10^{-8}$M) | 55.8 |
| NPY + $IP_3$ ($10^{-7}$M) | 39.6 |
| NPY + $IP_3$ ($10^{-6}$M) | 25.6 |

$IP_3$ demonstrates a significant decrease of the vasoconstriction induced by NPY also in very low concentrations. These effects imply a very potent inhibition of vessel constriction, which is a dominant component in diseases and conditions such as vasospasm, angina, stroke and hypertension.

EXAMPLE 2

In this experiment rats were used for an in vivo evaluation of the effects of NPY.

The animals were anaesthetized with pentobarbital and operated in such a way that the peripheral vasoconstriction can be studied without the normal compensatory behaviour of the central nervous system. Thus in this model direct effects for example on blood pressure when introducing substances influencing vasoconstriction can be measured.

Six animals were used as a control group. These animals were given an injection of saline just before another injection of 1 mg/kg NPY. The medium blood pressure after the injection of NPY was measured to be 70 mm Hg.

To six other animals were given an injection of 20 mg/kg of D-myo-inositol-1.2-6-trisphosphate ($IP_3$) before the injection of NPY. Determination of the medium blood pressure in this group of animals gave a value of 15 mm Hg.

Thus $IP_3$ shows a significant effect on reducing NPY-induced vasoconstriction. These effects demonstrate a very potent effect of $IP_3$ to reduce vasoconstriction which is very beneficial in conditions like stroke, vasospasm and hypertension. The counteractive effect of $IP_3$ against NPY-related effects also implies a beneficial role in conditions such as depression; conditions where the neurotransmitter function is abnormal; abnormal food and drink intake; respiratory diseases and abnormal renal function.

EXAMPLE 3

Solution of sodium salt of D-myo-inositol-1.2.6-trisphosphate for injection.

0.5 g of the sodium salt of IP$_3$ and 0.77 g NaCl were dissolved in 98.73 ml of water for injection to form a solution suitable for injection into a person or an animal.

EXAMPLE 4

The effect of D-myo-inositol-1,2,6-trisphosphate (IP$_3$) to reduce gastrointestinal secretion was assessed in an experiment with rats.

Two groups of 9 animals in each were deprived of food 12 hrs before the experiment and were then anesthesized with pentobarbital (Nembutal®, 50 mg/kg). After a surgical operation in the gastrointestinal tract a 10 cm long jejunal segment was isolated with intact vascular supply. This segment, still in normal contact with the animal, was placed in a plastic chamber in such a way that the free passage of fluid in and out of the segment was allowed. The chamber was hanging approximately 5 mm above the abdominal wall of the animal and was connected to a force displacement transducer for measuring changes in intestinal weight. Net fluid transport (NFT) across the intestinal segment was continously recorded by connecting the force transducer to a Grass polygraph.

Pure cholera toxin (Sigma Chemicals), 20 µg, were dissolved in 0.5 ml saline (0.9% NaCl-solution) and was introduced into the intestinal lumen in each animal. Within three hours all animals developed a net fluid loss from the intestinal tissue into the lumen. After this period an infusion of IP$_3$ (60 mg/kg h) was administered to one group of the animals while the other group received saline via infusion.

The secretion from the intestinal segment, net fluid transport (NFT), measured as µl/min×100 cm$^2$, was determined for 30 minute periods during the infusion.

The data obtained are shown in the following table:

| time period after infusion start (mins) | NFT (µl/min × 100 cm$^2$) Control group | IP$_3$-treated group |
| --- | --- | --- |
| before infusion | 124 | 90 |
| 0-30 | 115 | 16 |
| 30-60 | 105 | 8 |
| 60-90 | 99 | 12 |
| 90-120 | 97 | 15 |
| 120-150 | 105 | 24 |
| 150-180 | 108 | 13 |

Thus a dramatic decrease in gastrointestinal secretion is achieved when treatment with IP$_3$ is performed.

We claim:

1. A method of treating abnormal renal function caused by abnormal levels of neuropeptide Y (NPY) comprising administering to a human or an animal in need thereof an effective amount of a pharmaceutical composition comprising at least one specific isomer of inositol triphosphate sufficient to treat abnormal renal function caused by abnormal levels of neuropeptide Y.

2. A method of treating abnormal renal function comprising administering to a human or an animal in need thereof an effective amount of a pharmaceutical composition comprising at least one specific isomer of inositol triphosphate sufficient to treat abnormal renal function caused by abnormal levels of neuropeptide Y.

3. A method according to claims 1 or 2 wherein the pharmaceutical composition comprises an inositoltriphosphate in salt form.

4. A method according to claim 3 wherein the salt of inositoltriphosphate is a salt of sodium, potassium, calcium or zinc.

5. A method according to claims 1 or 2 wherein the pharmaceutical composition is in tablet or granulated form.

6. A method according to claims 1 or 2 wherein the pharmaceutical composition is in the form of a solution.

7. A method according to claim 6 wherein the pharmaceutical composition comprises at least one isomer of inositoltrisphosphate selected from the group D-myo-inositol-1.2.6-trisphosphate, myo-inositol-1.2.3-trisphosphate and L-myo-inositol-1.3.4-trisphosphate.

8. A method of treating renal diseases by administering to a human or an animal a pharmaceutical composition comprising an effective amount of at least one isomer of inositoltrisphosphate and another pharmaceutically active compound effective in the renal area sufficient to obtain said treatment.

9. A method according to claim 8 wherein the composition is in a combined dosage form.

10. A method according to claim 8 wherein the composition is in a separate dosage form for separate or combined administration.

11. A method according to claim 8 wherein the isomer of inositoltriphosphate is D-myo-inositol-1.2.6-triphosphate.

* * * * *